United States Patent [19]

VanGemert

[11] Patent Number: 5,405,958
[45] Date of Patent: Apr. 11, 1995

[54] PHOTOCHROMIC SPIRO(INDOLINE)NAPHTHOXAZINE COMPOUNDS

[75] Inventor: Barry VanGemert, Murrysville, Pa.

[73] Assignee: Transitions Optical, Inc., Pinellas Park, Fla.

[21] Appl. No.: 993,587

[22] Filed: Dec. 21, 1992

[51] Int. Cl.$^6$ .............. G02B 27/00; C07D 265/00; C07D 295/00

[52] U.S. Cl. .............. 544/71; 359/647; 351/162; 351/163; 523/106; 523/135; 524/90; 524/97

[58] Field of Search .............. 544/71; 359/647; 351/162, 163; 523/106, 135; 524/90, 97

[56] References Cited

U.S. PATENT DOCUMENTS

| | | | |
|---|---|---|---|
| 3,562,172 | 2/1971 | Ono et al. | 252/300 |
| 3,567,605 | 3/1971 | Becker | 204/158 |
| 3,578,602 | 5/1971 | Ono et al. | 252/300 |
| 4,215,010 | 7/1980 | Hovey et al. | 252/300 |
| 4,342,668 | 8/1982 | Hovey et al. | 252/586 |
| 4,360,653 | 11/1982 | Stevens et al. | 526/301 |
| 4,637,698 | 1/1987 | Kwak et al. | 351/163 |
| 4,719,296 | 1/1988 | Irie et al. | 544/71 |
| 4,719,296 | 1/1988 | Irie et al. | 544/71 |
| 4,720,547 | 1/1988 | Kwak et al. | 544/71 |
| 4,913,544 | 4/1990 | Rickwood | 351/163 |
| 4,968,454 | 11/1990 | Crano et al. | 252/586 |
| 4,994,208 | 2/1991 | McBain et al. | 252/586 |
| 5,021,196 | 6/1991 | Crano et al. | 252/586 |
| 5,066,818 | 11/1991 | Van Gemert et al. | 549/389 |

FOREIGN PATENT DOCUMENTS

WO85/02619 6/1985 WIPO .

OTHER PUBLICATIONS

E. T. Jarvi et al, "1,8,17,24–Tetraoxa[8.8](2,6)naphthalenophane 3,5,19,21–tetrayne–10,30–dicarboxylic Acid Derivatives, Novel Complexors of Aromatic Guests", J. Am. Chem. Soc. 1982, 104, 7196–7204.

*Primary Examiner*—Mukund J. Shah
*Assistant Examiner*—Matthew V. Grumbling
*Attorney, Agent, or Firm*—Irwin M. Stein

[57] ABSTRACT

Described are novel reversible photochromic spiro(indoline) naphthoxazine compounds of improved photocolorability that may be graphically represented by the formula,

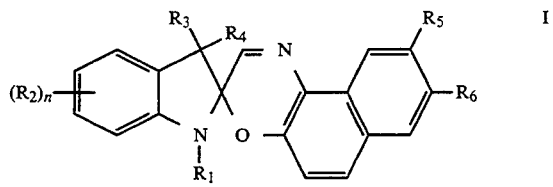

In preferred embodiments, $R_1$ is allyl, alkoxyalkyl, and alkyl; each $R_2$ is alkyl or alkoxy; $R_3$ and $R_4$ are alkyl; $R_5$ is alkoxycarbonyl; and $R_6$ is hydroxy, alkoxy, or carboxy, e.g., acetoxy. Also described are organic host materials that contain or that are coated with such compounds. Articles such as ophthalmic lenses or other plastic transparencies that incorporate the naphthoxazine compounds or combination thereof with complementary photochromic compounds, e.g., naphthopyran or benzopyran compounds, are also described.

19 Claims, No Drawings

PHOTOCHROMIC SPIRO(INDOLINE)NAPHTHOXAZINE COMPOUNDS

DESCRIPTION OF THE INVENTION

The present invention relates to certain novel spiro-(indoline)naphthoxazine compounds. More particularly, this invention relates to novel photochromic spiro(indoline) naphthoxazine compounds, and to compositions and articles containing such novel naphthoxazine compounds. When subjected to ultraviolet irradiation, photochromic compounds become activated and change light transmission properties. Subsequently, activated reversible photochromic compounds revert to their original color or inactivated state when the initial ultraviolet light source is removed.

The photochromism of certain spiro(indoline)naphthoxazine compounds is well known and is disclosed, for example, in U.S. Pat. Nos. 3,562,172, 3,578,602, and 4,342,668. The compounds described in U.S. Pat. Nos. 3,562,172 and 3,578,602 are naphthoxazine derivatives with substituents on the indoline portion of the molecule. U.S. Pat. No. 4,342,668 describes naphthoxazine derivatives with substituents on the 8' or 9' position, one of which substituents is halogen or lower alkoxy—the other being hydrogen. These compounds have been described as having enhanced photocolorability, i.e., a relatively large change in optical density between the activated and inactivated state.

The present invention relates to novel spiro(indoline) naphthoxazines which have been found to have improved photocolorability and an unexpectedly higher absorption maxima than the corresponding unsubstituted compounds. These compounds have certain substituents on the 8' and 9' positions of the naphthoxazine portion of the molecule.

DETAILED DESCRIPTION OF THE INVENTION

In recent years, photochromic plastic materials, particularly plastic materials for optical applications, have been the subject of considerable attention. In particular, photochromic ophthalmic plastic lenses have been investigated because of the weight advantages they offer, vis-a-vis, glass lenses. Moreover, photochromic transparencies for vehicles such as cars and airplanes have been of interest because of the potential safety features that such transparencies offer.

Ideally, photochromic compounds used in optical applications, such as conventional ophthalmic lenses, are those which possess (a) a high quantum efficiency for coloring in the near ultraviolet, (b) a low quantum yield for bleaching with white light and (c) a relatively fast thermal fade at ambient temperature but not so rapid a thermal fade rate that the combination of white light bleaching and thermal fade prevent coloring by the ultraviolet component of strong sunlight.

In accordance with the present invention, certain novel spiro(indoline)naphthoxazine compounds having a high quantum efficiency for coloring in the near ultraviolet, improved photocolorability and an acceptable rate of fade have been discovered. These compounds may be graphically represented by the following graphic Formula I:

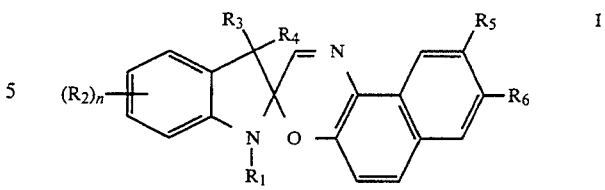

In graphic formula I, $R_1$ may be a $C_1-C_8$ alkyl, phen(-$C_1-C_4$)alkyl, naphth($C_1-C_4$)alkyl, allyl, acrylyloxy($C_2-C_6$)alkyl, methacrylyloxy($C_2-C_6$)alkyl, $C_1-C_4$ acyloxy($C_2-C_6$)alkyl, carboxy($C_2-C_6$)alkyl, cyano($C_2-C_6$)alkyl, hydroxy($C_2-C_6$)alkyl, $C_1-C_6$ alkoxy($C_2-C_4$)alkyl or $(C_2H_4O)_m \cdot CH_3$, wherein m is an integer from 1 to 6. Preferably, $R_1$ is allyl, $C_1-C_3$ alkoxy($C_2-C_4$)alkyl or $C_1-C_4$ alkyl, e.g., methyl, ethyl, propyl or butyl. Each $R_2$ may be a $C_1-C_5$ alkyl, $C_1-C_5$ alkoxy, nitro, cyano, $C_1-C_8$ alkoxycarbonyl, $C_1-C_4$ acyloxy, halo, $C_1-C_4$ monohaloalkyl or $C_1-C_4$ polyhaloalkyl. Preferably, $R_2$ is $C_1-C_3$ alkoxy, e.g., methoxy, ethoxy or propoxy, or $C_1-C_3$ alkyl, e.g., methyl, ethyl or propyl. The halogen and halo substituents may be chloro, fluoro, iodo or bromo, preferably chloro or fluoro, and n is the integer 0, 1 or 2.

$R_3$ and $R_4$ may each be $C_1-C_5$ alkyl, benzyl, phenyl, mono- or di-substituted phenyl, said phenyl substituents being $C_1-C_5$ alkyl or $C_1-C_5$ alkoxy, or $R_3$ and $R_4$ may together form a cyclic ring containing from 5 to 8 carbon atoms which includes the spiro carbon atom, norbornyl or adamantyl. Preferably, each $R_3$ and $R_4$ is a $C_1-C_3$ alkyl, i.e., methyl, ethyl or propyl, or $R_3$ and $R_4$ may together form a cyclic ring containing from 5 to 7 carbon atoms which includes the spiro carbon atom.

$R_5$ is the group $-C(O)X$, wherein X is the group $-OR_7$ or $-N(R_8)R_9$, wherein $R_7$ is selected from $C_1-C_6$ alkyl, benzyl, $C_1-C_6$ alkyl substituted benzyl, $C_1-C_6$ alkoxy substituted benzyl, $C_1-C_6$ alkoxy($C_2-C_4$)alkyl, allyl, or $C_1-C_6$ mono- or di-haloalkyl, e.g., chloro, fluoro, bromo and iodoalkyl, particularly chloro- and fluoroalkyl, and wherein $R_8$ and $R_9$ are each selected from hydrogen, $C_1-C_5$ alkyl, $C_5-C_7$ cycloalkyl, phenyl, and substituted phenyl, or $R_8$ and $R_9$ may together with the nitrogen form a substituted or unsubstituted heterocyclic ring having from 5 to 6 ring atoms, which ring includes the nitrogen atom, and optionally one additional hetero atom of nitrogen or oxygen, said phenyl and heterocyclic ring substitutents being $C_1-C_5$ alkyl or $C_1-C_6$ alkoxy. Preferably $R_7$ is allyl or $C_1-C_3$ alkyl, e.g., methyl, ethyl, propyl, butyl, pentyl or hexyl.

$R_6$ is the group, $-O-Y$, wherein Y may be hydrogen, $C_1-C_6$ alkyl, benzyl, $C_1-C_6$ alkyl substituted benzyl, $C_1-C_6$ alkoxy substituted benzyl, $C_1-C_6$ alkoxy($C_2-C_4$)alkyl, $C_1-C_6$ haloalkyl, e.g., chloro, fluoro, bromo or iodoalkyl, allyl or the group, $-C(O)Z$, wherein Z is $C_1-C_6$ alkyl, phenyl, $C_1-C_6$ alkyl substituted phenyl, $C_1-C_6$ alkoxy substituted phenyl, $C_1-C_6$ alkoxy, phenoxy, $C_1-C_6$ alkyl substituted phenoxy, $C_1-C_6$ alkoxy substituted phenoxy, $C_1-C_6$ alkylamino, phenylamino, $C_1-C_6$ alkyl substituted phenylamino or $C_1-C_6$ alkoxy substituted phenylamino. Preferably $R_6$ is the group, $-O-Y$, wherein Y is hydrogen, $C_1-C_3$ alkyl or the group, $-C(O)Z$, wherein Z is $C_1-C_3$ alkyl, e.g., methyl. As used in the specification and claims herein, the term alkyl is intended to include linear and branched alkyls.

Compounds represented by graphic formula I may be prepared by esterification of the carboxylic acid group of 3,7-dihydroxy-2-naphthoic acid using sodium bicarbonate and the corresponding $R_7$ halide, e.g., alkyl halide, such as methyl iodide, in dimethylformamide (DMF) followed by nitrosation using sodium nitrite and acetic acid in methylene chloride to yield the corresponding 3,7-dihydroxy-8-nitroso naphthoate. To prepare the corresponding amide, the ester may be reacted with the appropriate primary or secondary amine or ammonia followed by nitrosation as described above. Condensation of this material with a Fisher's Base, as shown in the following equation, produces the corresponding spiro(indoline)naphthoxazine. This naphthoxazine may be subjected to further reactions, such as alkylation or acylation, to produce the desired $R_6$ substituent at the 8' position.

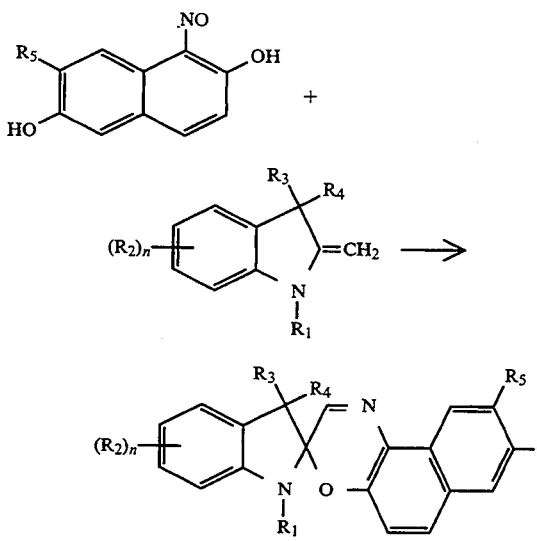

On irradiation of the compounds of graphic formula I with ultraviolet light, the naphthoxazine ring is reported to open reversibly at the carbon-oxygen bond between the spiro carbon atom and the ring oxygen., The formation of the open form of the colorless compound is believed to be responsible for the coloring observed on exposure to ultraviolet light. It is also believed that the extension of the chromophore by the claimed substituents on the 8' and 9' positions may be responsible for the improved photocolorability and the bathochromic shift in the UV spectrum relative to the naphthoxazine compounds disclosed in U.S. Pat. No. 4,342,668. The colored form of the photochromic compounds of graphic formula I fade to the colorless state at normal ambient temperatures when the ultraviolet light source is removed. Compounds represented by graphic formula I may be used alone or in combination with other photochromic compounds in those applications in which organic photochromic substances may be employed, such as optical lenses, e.g., ophthalmic and plano lenses, face shields, goggles, visors, camera lenses, windows, automotive windshields, aircraft and automotive transparencies, e.g., T-roofs, sidelights and backlights, plastic films and sheets, novelty items, e.g., toys and posters, textiles and coatings, e.g., coating compositions such as paints, and verification marks on security documents, e.g.,, documents such as banknotes, passports and drivers' licenses for which authentication or verification of authenticity may be desired. Naphthoxazines represented by graphic formula I exhibit color changes from colorless to colors ranging from green to blue.

Examples of particularly contemplated naphthoxazines are the following:

(1) 1,3,3,4,5( or 1,3,3,5,6,)-pentamethyl-9'-methoxycarbonyl-8'-hydroxy-spiro[indoline-2,3'-[3H]naphth[2,1-b][1,4]oxazine]

(2) 1-propyl-B,3,4,5(or 3,3,5,6)-tetramethyl-9'-methoxycarbonyl-8'-hydroxy-spiro[indoline-2,3'-[3H]naphth[2,1-b][1,4]oxazine]

(3) 1,3,3,4,5( or 1,3,3,5,6,)-pentamethyl-9'-methoxycarbonyl-8'-methoxy-spiro[indoline-2,3'-[3H]naphth[2,1-b][1,4]oxazine]

(4) 1-propyl-3,B,4,5(or 3,3,5,6)-tetramethyl-9'-methoxycarbonyl-8'-methoxy-spiro[indoline-2,3'-[3H]naphth[2,1-b][1,4]oxazine](5) 1,3,3,4,5( or 1,3,3,5,6,)-pentamethyl-9'-methoxycarbonyl-8'-acetoxy-spiro[indoline-2,3'-[3H]naphth[2,1-b][1,4]oxazine]

(6) 1-propyl-B-ethyl-B-methyl-9'-methoxycarbonyl-8'-acetoxy-spiro[indoline-2,3'-[3H]naphth[2,1-b][1,4]oxazine]

(7) 1-propyl-3,3-dimethyl-5-methoxy-9'-methoxycarbonyl-8'-acetoxy-spiro[indoline-2,3'-[3H]naphth[2,1-b][1,41oxazine]

(8) 1-propyl-3,3,4,5(or 3,3,5,6)-tetramethyl-9'-methoxycarbonyl-8'-acetoxy-spiro[indoline-2,3'-[3H]naphth[2,1-b][1,4]oxazine]

(9) 1-methoxyethyl-3,3-dimethyl-9'-allyloxycarbonyl-8'-benzoyloxy-spiro[indoline-2,3'-[3H]naphth[2,1-b][1,4]oxazine]

(10) 1-allyl-3,3-spirocyclohexyl-9'-benzyloxycarbonyl-8'-chloroacetoxy-spiro[indoline-2,3'-[3H]naphth[2,1-b][1,4]oxazine]

Commercially available photoreactive inorganic glass lenses containing silver halide particles darken to a neutral color, such as gray or brown, in unfiltered sunlight. In order to duplicate this color change in a plastic lens using the organic photochromic naphthoxazines of graphic formula I, it is contemplated that such naphthoxazines be used in combination with other appropriate complementary organic photochromic materials so that together they produce the desired gray or brown color shade when the plastic lens containing such photochromic materials is exposed to ultraviolet light.

For example, a compound which colors to yellow may be blended with a compound that colors to an appropriate purple to produce a brown shade. Similarly, a compound which is orange in its colored state will produce a shade of gray when used in conjunction with an appropriate blue coloring compound. Also contemplated is the use of various combinations of photochromic compounds that color orange, yellow, blue, and purple with naphthoxazine compounds of graphic formula I to produce the desired neutral color. U.S. Pat. No. 4,968,454 describes how two (or more) organic photochromic substances can be combined to produce variable light transmittance articles, such as ophthalmic lens.

The relative amounts of naphthoxazine compounds of graphic formula I and other complementary organic photochromic compounds used in combination will vary and depend in part upon the relative intensities of the color of the activated species of such compounds, and the ultimate color desired. Generally, the weight ratio of the aforedescribed naphthoxazine compound(s)

to the other complementary photochromic compound(s) will vary from about 1:3 to about 3:1, e.g., between about 0.75:1 and about 2:1.

Particularly contemplated classes of complementary organic photochromic compounds that may be used with the naphthoxazines of the present invention include: spiro(indoline)-type compounds such as other spiro(indoline) naphthoxazines, spiro(benzindoline)-naphthoxazines, spiro(indoline)pyridobenzoxazines, spiro(benzindoline)pyridobenzoxazines, spiro(indoline)-naphthopyrans, spiro(benzindoline)naphthopyrans, spiro(indoline)benzopyrans, spiro(indoline)benzoxazines, spiro(benzindoline)benzoxazines, chromenes, e.g., benzopyrans and naphthopyrans, metal dithizonate compounds, fulgides or fulgimides and spiro(di)hydroindolizines.

More particularly, the contemplated classes of complementary organic photochromic compounds include the naphthopyran photochromic compounds disclosed in U.S. Pat. No. 5,066,818, which color to yellow-orange when activated; spiro(indoline)pyridobenzoxazine photochromic compounds described in U.S. Pat. Nos. 4,637,698 and 4,720,547; and spiro(indoline) naphthoxazines described in U.S. Pat. Nos. 3,562,172, 3,578,602, 4,215,010 and 4.,342,668, which are reported to color to blue when activated. See the disclosure of U.S. Pat. No. 5,066,818 from column 6, line 30 to column 13, line 34, which may be incorporated herein, for examples of the aforesaid spiro(indoline) type compounds.

Photochromic compounds of the present invention, mixtures of such compounds with other photochromic compounds, or compositions containing same (hereinafter "photochromic substances") may be applied to or incorporated into a host material by various methods described in the art. Such methods include dissolving or dispersing the substance within the host material, e.g., imbibition of the photochromic substance into the host material by immersion of the host material in a hot solution of the photochromic substance or by thermal transfer; providing the photochromic substance as a separate layer between adjacent layers of the host material, e.g., as a part of a polymer film; and applying the photochromic substance as part of a coating placed on the surface of the host material. The term "imbibition" or "imbibe" is intended to mean and include permeation of the photochromic substance alone into the host material, solvent assisted transfer absorption of the photochromic substance into a porous polymer, vapor phase transfer, and other such transfer mechanisms.

The amount of photochromic substance or composition-containing same applied to or incorporated into a host material is not critical provided that a sufficient amount is used to produce a photochromic effect discernible to the naked eye upon activation. Generally such amount can be described as a photochromic amount. The particular amount used depends often upon the intensity of color desired upon irradiation thereof and upon the method used to incorporate or apply the photochromic substances. Typically, the more compound applied or incorporated, the greater is the color intensity. Generally, the amount of each photochromic substance incorporated into or applied to a photochromic optical host material may range from about 0.15 to about 0.35 milligrams per square centimeter of surface to which the photochromic substance(s) is incorporated or applied.

Compatible (chemically and color-wise) tints, i.e., dyes, may be applied to the host material to achieve a more aesthetic result, for medical reasons, or for reasons of fashion. The particular dye selected will vary and depend on the aforesaid need and result to be achieved. In one embodiment, the dye may be selected to complement the color resulting from the activated photochromic substances, e.g., to achieve a more neutral color or absorb a particular wavelength of incident light. In another embodiment, the dye may be selected to provide a desired hue to the host matrix when the photochromic substances is in an inactivated state.

The polymer host material will usually be transparent, but may be translucent or even opaque. The polymer product need only be transparent to that portion of the electromagnetic spectrum, which activates the photochromic substance, i.e., that wavelength of ultraviolet (UV) light that produces the open form of the substance and that portion of the visible spectrum that includes the absorption maximum wavelength of the substance in its UV activated form, i.e., the open form. Further, the resin color should not be such that it masks the color of the activated form of the photochromic substance, i.e., so the change in color is readily apparent to the observer. Preferably, the host material article is a solid transparent or optically clear material.

Examples of host materials which may be used with the photochromic substances or compositions described herein include: polymers, i.e.,. homopolymers and copolymers, of polyol(allyl carbonate) monomers, polymers, i.e., homopolymers and copolymers, of polyfunctional acrylate monomers, polyacrylates, poly(alkylacrylates) such as poly(methyl methacrylate), cellulose acetate, cellulose triacetate, cellulose acetate propionate, cellulose acetate butyrate, poly(vinyl acetate), poly(vinyl alcohol), poly(vinyl chloride), poly(vinylidene chloride), polyurethanes, polycarbonates, poly(ethylene terephthalate), polystyrene, copoly(styrene-methylmethacrylate), copoly(styrene-acrylonitrile), polyvinylbutyral and polymers, i.e., homopolymers and copolymers, of diallylidene pentaerythritol, particularly copolymers with polyol (allyl carbonate) monomers, e.g., diethylene glycol bis(allyl carbonate), and acrylate monomers. Blends of transparent polymers are also suitable as host materials.

Preferably, the host material is an optically clear polymerized organic material prepared from a polycarbonate resin, such as the carbonate-linked resin derived from bishpenol A and phosgene, which is sold under the trademark, LEXAN; a poly(methyl methacrylate), such as the material sold under the trademark, PLEXIGLAS; polymerizates of a polyol(allyl carbonate) monomer, especially diethylene glycol bis(allyl carbonate), which monomer is sold under the trademark, CR-39, and polymerizates of copolymers of a polyol (allyl carbonate), e.g., diethylene glycol bis(allyl carbonate), with other copolymerizable monomeric materials, such as copolymers with vinyl acetate, e.g., copolymers of from 80–90 percent diethylene glycol bis(allyl carbonate) and 10–20 percent vinyl acetate, particularly 80–85 percent of the bis(allyl carbonate) and 15–20 percent vinyl acetate, and copolymers with a polyurethane having terminal diacrylate functionality, as described in U.S. Pat. Nos. 4,360,653 and 4,994,208; cellulose propionate, cellulose butyrate, cellulose acetate butyrate, polystyrene and copolymers of styrene with methyl methacrylate, vinyl acetate and acrylonitrile.

The present invention is more particularly described in the following examples which are intended as illustrative only, since numerous modifications and variations therein will be apparent to those skilled in the art.

EXAMPLE 1

Step 1

Sixty grams (0.3 mole) of 3,7-dihydroxy-2-naphthoic acid and 42 grams (0.5 mole) of sodium bicarbonate were suspended with stirring in 250 milliliters of dimethylformamide (DMF) in a 500 milliliter round bottom flask equipped with a reflux condenser and nitrogen pad. The mixture was warmed to 60° C. and held there for 2 hours. Afterwards, the mixture was cooled to room temperature and methyl iodide (57 grams, 0.4 mole) was added. The stirred reaction was then gradually warmed to 70° C. where it was kept for 2 hours. Subsequently, the contents of the flask were poured into four volumes of ice and water to precipitate the product. The resulting yellow solid was suction filtered and washed. with a sodium bicarbonate solution in order to remove any unreacted starting material. The yellow solid was next washed with water and air dried. High-performance liquid chromatographic (HPLC) analysis revealed that the solid consisted of two products. The yield of methyl 3,7-dihydroxy-2-naphthoate, which contained a small amount of methyl monohydroxy naphthoate, was 57 grams.

Step 2

Methyl 3,7-dihydroxy-2-naphthoate (21.8 grams, 0.1 mole) from Step 1 was suspended with stirring in 200 milliliters of methylene chloride containing 6 grams of acetic acid. The mixture was cooled to 0° C. Eight grams of sodium nitrite, as an aqueous solution, was added dropwise over a period of thirty minutes. The mixture was stirred an additional 2 hours at 5° C. and then vacuum filtered. The resulting solid product was washed with methylene chloride and then slurried in water. The solid was again suction filtered and air dried until a constant weight was obtained. The resulting yield of methyl 3,7-dihydroxy-8-nitroso-2-naphthoate was 24 grams.

Step 3

0.01 mole of 1,2,3,3,4,5(or 1,2,3,3,5,6)-hexamethyl indolium iodide (Fisher's base precursor) in 100 milliliters of chloroform was mixed with 100 milliliters of a 10 weight percent aqueous sodium hydroxide solution and the two phase system stirred vigorously for 15 minutes. At this point the chloroform layer was separated and washed two times with water. 0.01 mole of product prepared in Step 2 was added to the 0.01 mole of Fisher's base solution in the washed chloroform layer. The mixture was stirred and refluxed under nitrogen overnight. The resulting dark solution was then cooled and passed through a silica plug contained in a filtering funnel. The silica plug was washed with 50 milliliters of chloroform. The filtrate and the washings were combined and the solvent was removed by using a rotary evaporator. Addition of 20 milliliters of a 2:1 hexane:ethyl acetate solution resulted in the rapid crystallization of the product. The crystals were suction filtered and washed with a small amount of fresh solvent.

The recovered crystalline product (2.3 grams), hereinafter designated the principal product of Example 1, melted at 221°–222° C., was 94% pure, as determined by HPLC analysis, and had a nuclear magnetic resonance (NMR) spectrum that was consistent with the product, 1,3,3,4,5(or 1,3,3,5,6,)-pentamethyl-9'-methoxycarbonyl-8'-hydroxy-spiro[indoline-2,3'-[3H]naphth[2,1-b][1,4]oxazine]. Of particular note is that a diethylene glycol dimethyl ether solution of the product had a slight yellow cast but changed to green when irradiated with ultraviolet light. The solution returned to its original slightly colored condition after the ultraviolet light was removed.

Additional products were prepared by using the aforedescribed procedure with different Fisher's base precursors. The melting point range (MPR) was determined for each product. The resulting products and their MPR included the following:

1,3,3-trimethyl-9'-methoxycarbonyl-8'-hydroxy-spiro[indoline-2,3'-[3H]naphth[2,1-b][1,4]oxazine], MPR of 237°–238° C.;

1-propyl-3-ethyl-3-methyl-9'-methoxycarbonyl-8'-hydroxy-spiro[indoline-2,3'-[3H]naphth[2,1-b][1,4]oxazine], MPR of 178°–180° C.;

1-propyl-3,3-dimethyl-5-methoxy-9'-methoxycarbonyl-8'-hydroxy-spiro [indoline-2,3'-[3H]naphth[2,1-b][1,4]oxazine], MPR of 228–229° C.; and 1-propyl-3,3,4,5(or 3,3,5,6)-tetramethyl-9'-methoxycarbonyl-8'-hydroxy-spiro[indoline-2,3'-[3H]naphth[2,1-b][1,4]oxazine], MPR of 197°–199° C.

EXAMPLE 2

Two grams of the principal product of Example 1 were taken up in 100 milliliters of reagent grade acetone, One and one-half grams each of dimethyl sulfate and powdered potassium carbonate were added to the acetone solution and the stirred mixture refluxed overnight under a nitrogen pad, The acetone was removed by using a rotary evaporator and 50 milliliters each of water and methylene chloride was added, The mixture was stirred for 15 minutes to destroy excess dimethyl sulfate. The methylene chloride layer was separated, washed once with water, and the solvent removed on a rotary evaporator. The resulting residue was dissolved in a small amount of chloroform, placed on a silica column and eluted with a 2:1 mixture of hexane:ethyl acetate. The photochromic fractions were combined and the solvent was removed by using a rotary evaporator. The product began to precipitate as yellow crystals during the evaporation procedure. The crystals were collected by vacuum filtration and washed with a few milliliters of the hexane:ethyl acetate mixture.

The recovered crystalline product (1.8 grams), hereinafter designated the principal product of Example 2, melted at 218°–220° C., was 97% pure as determined by HPLC analysis, and had a nuclear magnetic resonance (NMR) spectrum that was consistent with the product, 1,3,3,4,5(or 1,3,3,5,6,)-pentamethyl-9'-methoxycarbonyl-8'-methoxy-spiro[indoline-2,3'-[3H]naphth[2,1-b][1,4]oxazine]. A diethylene glycol dimethyl ether solution of the product was colorless but changed to blue when irradiated with ultraviolet light. The solution returned to its original colorless condition after the ultraviolet light was removed.

Additional products were prepared by using the aforedescribed procedure with products prepared in Example 1 from different Fisher's base precursors. The melting point range (MPR) was determined for each product. The resulting products and their MPR included the following:

1,3,3-trimethyl-9'-methoxycarbonyl-8'-methoxy-spiro[indoline-2,3'-[3H]naphth[2,1-b][1,4]oxazine], MPR of 213°–215° C.;

1-propyl-3-ethyl-3-methyl-9'-methoxycarbonyl-8'-methoxy-spiro[indoline-2,3'-[3H]naphth[2,1-b][1,4]oxazine], MPR of 149°–150° C.;

1-propyl-B,B-dimethyl-5-methoxy-9'-methoxycarbonyl-8'-methoxy-spiro[indoline-2,3'-[3H]naphth[2,1-b][1,4]oxazine], MPR of 176°–177° C.; and 1-propyl-3,3,4,5(or 3,3,5,6)-tetramethyl-9'-methoxycarbonyl-8'-methoxy-spiro[indoline-2,3'-[3H]naphth[2,1-b][1,4]oxazine], MPR of 196°–198° C.

EXAMPLE 3

One and one-half grams of the principal product of Example 1 was dissolved in 75 milliliters of methylene chloride along with 2 grams of triethylamine and 100 milligrams of dimethylamino pyridine (DMAP). Fifty milliliters of a 10 weight percent aqueous sodium hydroxide solution was added and the two phase mixture cooled in an ice bath. Two grams of acetyl chloride (an excess) was then added dropwise to the rapidly stirred mixture. After five minutes, TLC analysis showed that a new (lower) photochromic spot had formed and that the starting material was completely gone. The organic phase was separated and washed twice with water followed by removal of the methylene chloride using a rotary evaporator. The residual oil readily crystallized. The crystalline product was broken into pieces, washed with hexane, suction filtered and dried.

The recovered crystalline product (1.5 grams), hereinafter designated the principal product of Example 3, melted at 175°–178° C., was 98% pure as determined by HPLC analysis, and had a nuclear magnetic resonance (NMR) spectrum that was consistent with the product, 1,3,3,4,5(or 1,3,3,5,6,)-pentamethyl-9'-methoxy-carbonyl-8'-acetoxy-spiro[indoline-2,3'-[3H]naphth[2,1-b][1,4]oxazine]. A diethylene glycol dimethyl ether solution of the product was colorless but changed to blue when irradiated with ultraviolet light. The solution returned to its original colorless condition after the ultraviolet light was removed.

Additional products were prepared by using the aforedescribed procedure with products prepared in Example 1 from different Fisher's base precursors. The melting point range (MPR) was determined for each product. The resulting products and their MPR included the following:

1,3,3-trimethyl-9'-methoxycarbonyl-8'-acetoxy-spiro[indoline-2,3'-[3H]naphth[2,1-b][1,4]oxazine], MPR of 165°–166° C.;

1-propyl-3-ethyl-3-methyl-9'-methoxycarbonyl-8'-acetoxy-spiro[indoline-2,3'-[3H]naphth[2,1-b][1,4]oxazine], MPR of 114°–116° C.;

1-propyl-3,3-dimethyl-5-methoxy-9'-methoxycarbonyl- 8'-acetoxy-spiro[indoline-2,3'-[3H]naphth[2,1-b][1,4]oxazine], MPR of 140°–141.5° C.; and 1-propyl-3,3,4,5(or 3,3,5,6)-tetramethyl-9'-methoxycarbonyl-8'-acetoxy-spiro[indoline-2,3'-[3H]naphth[2,1-b][1,4]oxazine], MPR of 126°–127° C.

EXAMPLE 4

The principal products of Examples 1, 2 and 3 were dissolved in diethylene glycol dimethyl ether. The concentrations of the resulting solutions were approximately 0.5 milligrams per milliliter. Each solution was tested in a UV spectrophotometer to determine its lambda max. The lambda max reported in Table 1 is the wavelength in the ultraviolet range closest to the visible spectrum or in the threshold range, i.e., 390 to 410 nanometers, of the visible spectrum, at which the maximum absorption and activation of the photochromic compound occurs in diethylene glycol dimethyl ether.

Comparative testing was conducted on the principle product of Example 3 and certain photochromic compounds described in U.S. Pat. Nos. 4,342,668 and 4,637,698. These compounds were imbibed by thermal transfer into test squares of a polymeric matrix prepared from a diethylene glycol bis(allyl carbonate) composition by the following procedure: Each photochromic compound was dissolved in toluene to form a 4 weight percent solution of the compound. A piece of No. 4 Whatman filter paper was saturated with the toluene solution of the photochromic compound and allowed to air dry. The dried filter paper was placed on one side of the polymer test square, which measured ⅛ inch (0.3 centimeter)×2 inch (5.1 centimeters)×2 inch (5.1 centimeters). A piece of untreated filter paper was placed on the other side of the polymer test square and the resulting sandwich placed between two plates of flat aluminum metal plates. The entire assembly was then placed in a 155° C. oven for a time sufficient to thermally transfer the photochromic compound into the polymer test square. Residence times in the oven were adjusted to imbibe comparable amounts of the photochromic compounds in order to yield a comparable UV absorbance at their lambda max. The imbibed test squares were washed with acetone after removal from the oven.

The imbibed polymer test squares were tested for photochromic response rates on an optical bench. The samples were illuminated by a 150 watt Xenon lamp fitted with a copper sulfate bath and a neutral density filter at an intensity of about one sun. A second beam of light provided by a filtered tungsten lamp arranged to pass through the sample area exposed by the UV source was used to monitor changes in transmission of the sample over different wavelength ranges in the visible region of the spectrum. The intensity of the monitoring beam after passing through the sample was measured by means of an IL-1500 radiometer equipped with a silicon detector head and matching filters.

The Δ OD/min., which represents the sensitivity of the photochromic compound's response to UV light, was measured using photopic filters on the silicon detector. The response of the filtered detector approximated the luminosity curve. The Δ OD was measured over the first five (5) seconds of UV exposure, then expressed on a per minute basis. The saturation optical density (OD) was taken under identical conditions as the Δ OD/min., except UV exposure was continued for 20 minutes. The lambda max reported in Table 2 is the wavelength in the ultraviolet range closest to the visible spectrum or in the threshold range, i.e., 390 to 410 nanometers, of the visible spectrum at which the maximum absorption and activation of the photochromic compound occurs in the polymer matrix test squares.

The bleach rate T ½(sec.) is the time interval in seconds for the absorbance of the activated form of the photochromic compounds in the test polymer to reach one half the highest absorbance at 25.7±0.5° C. after removal of the source of activating light. Results are tabulated in Tables 1 and 2.

TABLE I

| PRINCIPAL PRODUCT OF | LAMBDA MAX |
|---|---|
| Example 1 | 403 |
| Example 2 | 383 |
| Example 3 | 374 |

TABLE 2

| COMPOUND SAMPLE | LAMBDA MAX | Δ OD/min. SENSITIVITY | Δ OD @ SATURATION | BLEACH RATE T ½ (SEC.) |
|---|---|---|---|---|
| A[1] | 336 | 0.15 | 0.11 | 70 |
| B[2] | 350 | 0.44 | 0.36 | 69 |
| C[3] | 374 | 0.46 | 0.42 | 136 |
| D[4] | 346 | 0.21 | 0.11 | 47 |

[1] 1-propyl-3,3,5,6-tetramethyl-9'-methoxy-spiro[indoline-2,3'-[3H]naphth[2,1-b][1,4]oxazine]; cf. Example III of U.S. Pat. No. 4,342,668.

[2] 1-propyl-3,3,5,6-tetramethyl-spiro[indoline-2,3'-[3H]pyrido-[3,2-f][1,4]benzoxazine]; cf. claim 2 of U.S. Pat. No. 4,637,698.

[3] 1-propyl-3,3,4,5(or 3,3,5,6)-tetramethyl-9'-methoxy-carbonyl-8'-acetoxy-spiro[indoline-2,3'-[3H]naphth[2,1-b]-[1,4]oxazine] (Example 3).

[4] 1-propyl-3,3,4,5(or 3,3,5,6)-tetramethyl-spiro[indoline-2,3'-[3H]naphth[2,1-b][1,4]oxazine].

The results in Table 1 for the principle products of Examples 1, 2 and 3 show the relatively high lambda max values of the photochromic naphthoxazine compounds of the present invention compared to those of compound samples A, B and D of Table 2. The results tabulated in Table 2 for compound C, the principal product of Example 3, as compared to the other compounds, show an improved sensitivity, higher optical density at saturation, and an acceptable bleach rate. Compound C also had an absorption maxima in the UV spectrum unexpectedly higher than compounds A, B and D.

Although the present invention has been described with reference to the specific details of particular embodiments thereof, it is not intended that such details be regarded upon the scope of the invention except insofar as to the extent that they are included in the accompanying claims.

I claim:

1. A naphthoxazine compound represented by the following graphic formula:

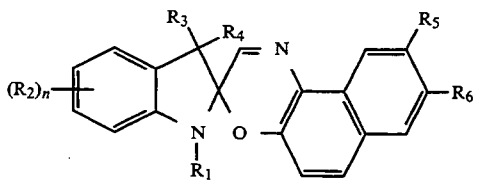

wherein:
(a) $R_1$ is $C_1$–$C_8$ alkyl, phen($C_1$–$C_4$)alkyl, naphth($C_1$–$C_4$)alkyl, allyl, acrylyloxy($C_2$–$C_6$)alkyl, methacrylyloxy($C_2$–$C_6$)alkyl, $C_1$–$C_4$ acyloxy($C_2$–$C_6$)alkyl, carboxy($C_2$–$C_6$)alkyl, cyano($C_2$–$C_6$)alkyl, hydroxy($C_2$–$C_6$)alkyl, $C_1$–$C_6$ alkoxy($C_2$–$C_4$)alkyl or $(C_2H_4O)_m$.$CH_3$, wherein m is an integer from 1 to 6;

(b) each $R_2$ is $C_1$–$C_5$ alkyl, $C_1$–$C_5$ alkoxy, nitro, cyano, $C_1$–$C_8$ alkoxycarbonyl, $C_1$–$C_4$ acyloxy, halo, $C_1$–$C_4$ monohaloalkyl or $C_1$–$C_4$ polyhaloalkyl;

(c) $R_3$ and $R_4$ are each $C_1$–$C_5$ alkyl, benzyl, phenyl, mono- or di-substituted phenyl, said phenyl substituents being $C_1$–$C_5$ alkyl or $C_1$–$C_5$ alkoxy, or $R_3$ and $R_4$ taken together form a group selected from a cyclic ring of from 5 to 8 carbon atoms which includes the spiro carbon atom, norbornyl or adamantyl;

(d) $R_5$ is the group —C(O)X, X being —OR$_7$ or —N(R$_8$)R$_9$, wherein R$_7$ is allyl, $C_1$–$C_6$ alkyl, benzyl, $C_1$–$C_6$ alkyl substituted benzyl, $C_1$–$C_6$ alkoxy substituted benzyl, $C_1$–$C_6$ alkoxy($C_2$–$C_4$)alkyl, or $C_1$–$C_6$ haloalkyl, and wherein R$_8$ and R$_9$ are each selected from hydrogen, $C_1$–$C_5$ alkyl, $C_5$–$C_7$ cycloalkyl, phenyl and substituted phenyl, or R$_8$ and R$_9$ together with the nitrogen form a substituted or unsubstituted saturated heterocyclic ring containing from 5 to 6 ring atoms, which ring includes as the hetero atom said nitrogen atom alone or one additional hetero atom of nitrogen or oxygen, said phenyl and heterocyclic ring substituents being selected from $C_1$–$C_5$ alkyl and $C_1$–$C_6$ alkoxy;

(e) $R_6$ is the group, —O—Y, wherein Y is hydrogen, $C_1$–$C_6$ alkyl, benzyl, $C_1$–$C_6$ alkyl substituted benzyl, $C_1$–$C_6$ alkoxy substituted benzyl, $C_1$–$C_6$ alkoxy($C_2$–$C_4$) alkyl, $C_1$–$C_6$ haloalkyl, allyl or the group, —C(O)Z, wherein Z is $C_1$–$C_6$ alkyl, phenyl, $C_1$–$C_6$ alkyl substituted phenyl, $C_1$–$C_6$ alkoxy substituted phenyl, $C_1$–$C_6$ alkoxy, phenoxy, $C_1$–$C_6$ alkyl substituted phenoxy, $C_1$–$C_6$ alkoxy substituted phenoxy, $C_1$–$C_6$ alkylamino, phenylamino, $C_1$–$C_6$ alkyl substituted phenylamino, or $C_1$–$C_6$ alkoxy substituted phenylamino; and (f) n is the integer 0, 1, or 2, said halo substituents being chloro, fluoro, iodo or bromo.

2. A naphthoxazine compound according to claim 1, wherein $R_1$ is allyl, $C_1$–$C_3$ alkoxy($C_2$–$C_4$)alkyl or $C_1$–$C_4$ alkyl; $R_3$ and $R_4$ are each $C_1$–$C_3$ alkyl or $R_3$ and $R_4$ taken together form a cyclic ring of from 5 to 7 carbon atoms which includes the spiro carbon atom; each $R_2$ is $C_1$–$C_3$ alkoxy or $C_1$–$C_3$ alkyl; X is the group, —OR$_7$, wherein $R_7$ is $C_1$–$C_3$ alkyl or allyl; and Y is hydrogen, $C_1$–$C_3$ alkyl or the group, —C(O)Z, wherein Z is $C_1$–$C_3$ alkyl.

3. A naphthoxazine compound according to claim 2, wherein $R_1$ is methyl or propyl; each $R_2$ is methoxy or methyl; $R_3$ and $R_4$ are each methyl or ethyl; $R_7$ is methyl; and Z is methyl.

4. A naphthoxazine compound wherein the compound is
(a) 1,3,3,4,5(or 1,3,3,5,6,)-pentamethyl-9'-methoxycarbonyl-8'-hydroxy-spiro[indoline-2,3'-[3H]naphth[2,1-b][1,4]oxazine];
(b) 1-propyl-3,3,4,5(or 3,3,5,6)-tetramethyl-9'-methoxy-carbonyl-8'-hydroxy-spiro[indoline-2,3'-[3H]naphth[2,1-b][1,4]oxazine];
(c) 1,3,3,4,5(or 1,3,3,5,6,)-pentamethyl-9'-methoxycarbonyl-8'-methoxy-spiro[indoline-2,3'-[3H]naphth[2,1-b][1,4]oxazine];

(d) 1-propyl-3,3,4,5(or 3,3,5,6)-tetramethyl-9'-methoxy-carbonyl-8'-methoxy-spiro[indoline-2,3'-[3H]naphth[2,1-b][1,4]oxazine];
(e) 1,3,3,4,5(or 1,3,3,5,6,)-pentamethyl-9'-methoxy-carbonyl-8'-acetoxy-spiro[indoline-2,3'-[3H]naphth[2,1-b][1,4]oxazine];
(f) 1-propyl-3-ethyl-3-methyl-9'-methoxy-carbonyl-8'-acetoxy-spiro[indoline-2,3'-[3H]naphth[2,1-b][1,4]oxazine];
(g) 1-propyl-3,3-dimethyl-5-methoxy-9'-methoxy-carbonyl-8'-acetoxy-spiro[indoline-2,3'-[3H]naphth[2,1-b][1,4]oxazine];
(h) 1-propyl-3,3,4,5(or 3,3,5,6)-tetramethyl-9'-methoxy-carbonyl-8'-acetoxy-spiro[indoline-2,3'-[3H]naphth[2,1-b][1,4]oxazine];
(i) 1-methoxyethyl-3,3-dimethyl-9'-allyloxy-carbonyl-8'-benzoyloxy-spiro[indoline-2,3,-[3H]naphth[2,1-b][1,4]oxazine]; or
(j) 1-allyl-3,3-spirocyclohexyl-9'-benzyloxycarbonyl-8'-chloroacetoxy-spiro[indoline-2,3,-[3H]naphth[2,1-b][1,4]oxazine].

5. A photochromic article comprising a polymeric host material and a photochromic amount of a naphthoxazine compound represented by the following graphic formula:

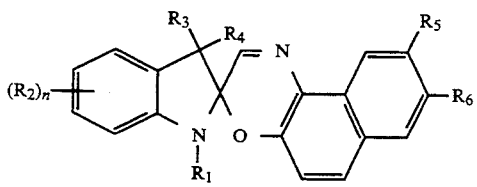

wherein:
(a) $R_1$ is $C_1$–$C_8$ alkyl, phen($C_1$–$C_4$)alkyl, naphth(-$C_1$–$C_4$)alkyl, allyl, acrylyloxy($C_2$–$C_6$)alkyl, methacrylyloxy($C_2$–$C_6$)alkyl, $C_1$–$C_4$ acyloxy($C_2$–$C_6$)alkyl, carboxy($C_2$–$C_6$)alkyl, cyano($C_2$–$C_6$)alkyl, hydroxy($C_2$–$C_6$)alkyl, $C_1$–$C_6$ alkoxy($C_2$–$C_4$)alkyl or ($C_2H_4O)_m$·$CH_3$, wherein m is an integer from 1 to 6;
(b) each $R_2$ is $C_1$–$C_5$ alkyl, $C_1$–$C_5$ alkoxy, nitro, cyano, $C_1$–$C_8$ alkoxycarbonyl, $C_1$–$C_4$ acyloxy, halo, $C_1$–$C_4$ monohaloalkyl or $C_1$–$C_4$ polyhaloalkyl;
(c) $R_3$ and $R_4$ are each $C_1$–$C_5$ alkyl, benzyl, phenyl, mono- or di-substituted phenyl, said phenyl substituents being $C_1$–$C_5$ alkyl or $C_1$–$C_5$ alkoxy, or $R_3$ and $R_4$ taken together form a group selected from a cyclic ring of from 5 to 8 carbon atoms which includes the spiro carbon atom, norbornyl or adamantyl;
(d) t{$_5$ is the group —C(O)X, X being —OR$_7$ or —N(R$_8$)R$_9$, wherein R$_7$ is allyl, $C_1$–$C_6$ alkyl, benzyl, $C_1$–$C_6$ alkyl substituted benzyl, $C_1$–$C_6$ alkoxy substituted benzyl, $C_1$–$C_6$ alkoxy($C_2$–$C_4$)alkyl, or $C_1$–$C_6$ haloalkyl, and wherein R$_8$ and R$_9$ are each selected from hydrogen, $C_1$–$C_5$ alkyl, $C_5$–$C_7$ cycloalkyl, phenyl and substituted phenyl, or R$_8$ and R$_9$ together with the nitrogen form a substituted or unsubstituted saturated heterocyclic ring containing from 5 to 6 ring atoms, which ring includes as the hetero atom said nitrogen atom alone or one additional hetero atom of nitrogen or oxygen, said phenyl and heterocyclic ring substituents being selected from $C_1$–$C_5$ alkyl and $C_1$–$C_6$ alkoxy;
(e) $R_6$ is the group, —O—Y, wherein Y is hydrogen, $C_1$–$C_6$ alkyl, benzyl, $C_1$–$C_6$ alkyl substituted benzyl, $C_1$–$C_6$ alkoxy substituted benzyl, $C_1$–$C_6$ alkoxy ($C_2$–$C_4$) alkyl, $C_1$–$C_6$ haloalkyl, allyl or the group, —C(O)Z, wherein Z is $C_1$–$C_6$ alkyl, phenyl, $C_1$–$C_6$ alkyl substituted phenyl, $C_1$–$C_6$ alkoxy substituted phenyl, $C_1$–$C_6$ alkoxy, phenoxy, $C_1$–$C_6$ alkyl substituted phenoxy, $C_1$–$C_6$ alkoxy substituted phenoxy, $C_1$–$C_6$ alkylamino, phenylamino, $C_1$–$C_6$ alkyl substituted phenylamino, or $C_1$–$C_6$ alkoxy substituted phenylamino; and
(f) n is the integer 0, 1, or 2, said halo substituents being chloro, fluoro, iodo or bromo.

6. The photochromic article of claim 5 wherein the host material is a polymer of polyol(allyl carbonate) monomers, polyacrylates, poly(alkylacrylates), polyfunctional acrylate monomers, cellulose acetate, cellulose triacetate, cellulose acetate propionate, cellulose acetate butyrate, poly(vinyl acetate), poly(vinyl alcohol), poly(vinyl chloride), poly(vinylidene chloride), polycarbonate, polyurethane, poly(ethylene terephthalate), polystyrene, copoly(styrene-methylmethacrylate), copoly(styrene.-acrylonitrile), polyvinylbutyral, or a polymer of diallylidene pentaerythritol.

7. The photochromic article of claim 6 wherein $R_1$ is allyl, $C_1$–$C_3$ alkoxy($C_2$–$C_4$)alkyl or $C_1$–$C_4$ alkyl; $R_3$ and $R_4$ are each $C_1$–$C_3$ alkyl or $R_3$ and $R_4$ taken together form a cyclic ring of from 5 to 7 carbon atoms which includes the spiro carbon atom; each $R_2$ is $C_1$–$C_3$ alkoxy or $C_1$–$C_3$ alkyl; X is the group, —OR$_7$, wherein R$_7$ is $C_1$–$C_3$ alkyl or allyl; and Y is hydrogen, $C_1$–$C_3$ alkyl or the group, —C(O)Z, wherein Z is $C_1$–$C_3$ alkyl.

8. The photochromic article of claim 7 wherein $R_1$ is methyl or propyl; each $R_2$ is methoxy or methyl; $R_3$ and $R_4$ are each methyl or ethyl; $R_7$ is methyl; and Z is methyl.

9. The photochromic article of claim 8 wherein the host material is a solid transparent homopolymer or copolymer of diethylene glycol bis(allyl carbonate), poly (4,4'dioxydiphenol-2,2-propane), poly(methylmethacrylate), polyvinylbutyral or a polyurethane.

10. The photochromic article of claim 9 wherein the photochromic compound is present in an amount of from about 0.15 to 0.35 milligrams per square centimeter of host material surface to which the photochromic substance(s) has been applied.

11. The photochromic article of claim 10 wherein the article is a lens.

12. A photochromic article comprising a solid transparent polymerized organic host material and a photochromic amount of each of (a) a first photochromic substance wherein said first photochromic substance is a spiro(indoline)naphthopyran, spiro (indoline)benzopyran, spiro (indoline) pyridobenzoxazine, spiro(indoline)-benzoxazine or a chromene, and (b) a naphthoxazine compound represented by the following graphic formula:

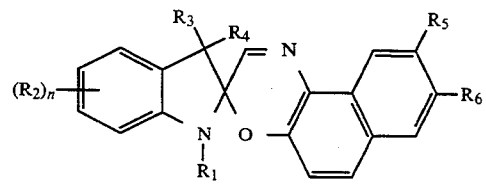

wherein:
(a) $R_1$ is $C_1$–$C_8$ alkyl, phen($C_1$–$C_4$)alkyl, naphth(-$C_1$–$C_4$)alkyl, allyl, acrylyloxy($C_2$–$C_6$)alkyl, methacrylyloxy($C_2$-$C_6$)alkyl, $C_1$-$C_4$ acyloxy($C_2$-$C_6$)alkyl, carboxy($C_2$-$C_6$)alkyl, cyano($C_2$-$C_6$)alkyl, hydroxy($C_2$-$C_6$)alkyl, $C_1$-$C_6$ alkoxy($C_2$-$C_4$)alkyl or ($C_2H_4O$)$_m$.$CH_3$, wherein m is an integer from 1 to 6;

(b) each $R_2$ is $C_1$-$C_5$ alkyl, $C_1$-$C_5$ alkoxy, nitro, cyano, $C_1$-$C_8$ alkoxycarbonyl, $C_1$-$C_4$ acyloxy, halo, $C_1$-$C_4$ monohaloalkyl or $C_1$-$C_4$ polyhaloalkyl;

(c) $R_3$ and $R_4$ are each $C_1$-$C_5$ alkyl, benzyl, phenyl, mono- or di-substituted phenyl, said phenyl substituents being $C_1$-$C_5$ alkyl or $C_1$-$C_5$ alkoxy, or $R_3$ and $R_4$ taken together form a group selected from a cyclic ring of from 5 to 8 carbon atoms which includes the spiro carbon atom, norbornyl or adamantyl;

(d) $R_5$ is the group —C(O)X, X being —$OR_7$ or —N($R_8$)$R_9$, wherein $R_7$ is allyl, $C_1$-$C_6$ alkyl, benzyl, $C_1$-$C_6$ alkyl substituted benzyl, $C_1$-$C_6$ alkoxy substituted benzyl, $C_1$-$C_6$ alkoxy($C_2$-$C_4$)alkyl, or $C_1$-$C_6$ haloalkyl, and wherein $R_8$ and $R_9$ are each selected from hydrogen, $C_1$-$C_5$ alkyl, $C_5$-$C_7$ cycloalkyl, phenyl and substituted phenyl, or $R_8$ and $R_9$ together with the nitrogen form a substituted or unsubstituted saturated heterocyclic ring containing from 5 to 6 ring atoms, which ring includes as the hetero atom said nitrogen atom alone or one additional hetero atom of nitrogen or oxygen, said phenyl and heterocyclic ring substituents being selected from $C_1$-$C_5$ alkyl and $C_1$-$C_6$ alkoxy;

(e) $R_6$ is the group, —O—Y, wherein Y is hydrogen, $C_1$-$C_6$ alkyl, benzyl, $C_1$-$C_6$ alkyl substituted benzyl, $C_1$-$C_6$ alkoxy substituted benzyl, $C_1$-$C_6$ alkoxy ($C_2$-$C_4$) alkyl, $C_1$-$C_6$ haloalkyl, allyl or the group, —C(O)Z, wherein Z is $C_1$-$C_6$ alkyl, phenyl, $C_1$-$C_6$ alkyl substituted phenyl, $C_1$-$C_6$ alkoxy substituted phenyl, $C_1$-$C_6$ alkoxy, phenoxy, $C_1$-$C_6$ alkyl substituted phenoxy, $C_1$-$C_6$ alkoxy substituted phenoxy, $C_1$-$C_6$ alkylamino, phenylamino, $C_1$-$C_6$ alkyl substituted phenylamino, or $C_1$-$C_6$ alkoxy substituted phenylamino; and (f) n is the integer 0, 1, or 2, said halo substituents being chloro, fluoro, iodo or bromo.

13. The photochromic article of claim 12 wherein the organic host material is polymer of polyol(allyl carbonate) monomers, polyacrylates, poly(alkylacrylates), polyfunctional acrylate monomers, cellulose acetate, cellulose triacetate, cellulose acetate propionate, cellulose acetate butyrate, poly(vinyl acetate), poly(vinyl alcohol), poly(vinyl chloride), poly(vinylidene chloride), polycarbonate, polyurethane, poly(ethylene terephthalate), polystyrene, copoly(styrene-methylmethacrylate), copoly(styrene-acrylonitrile), polyvinylbutyral, or a polymer of diallylidene pentaerythritol.

14. The photochromic article of claim 13 wherein $R_1$ is allyl, $C_1$-$C_3$ alkoxy($C_2$-$C_4$)alkyl or $C_1$-$C_3$ alkyl; $R_3$ and $R_4$ are each $C_1$-$C_3$ alkyl or $R_3$ and $R_4$ taken together form a cyclic ring of from 5 to 7 carbon atoms which includes the spiro carbon atom; each $R_2$ is $C_1$-$C_3$ alkoxy or $C_1$-$C_3$ alkyl; X is the group, —$OR_7$, wherein $R_7$ is $C_1$-$C_3$ alkyl or allyl; and Y is hydrogen, $C_1$-$C_3$ alkyl or the group, —C(O)Z, wherein Z is $C_1$-$C_3$ alkyl.

15. The photochromic article of claim 14 wherein $R_1$ is methyl or propyl; each $R_2$ is methoxy or methyl; $R_3$ and $R_4$ are each methyl or ethyl; $R_7$ is methyl; and Z is methyl.

16. The photochromic article of claim 15 wherein the organic host material is a solid transparent homopolymer or copolymer of diethylene glycol bis(allyl carbonate), poly (4,4'dioxydiphenol-2,2-propane), poly(methylmethacrylate), polyvinylbutyral or a polyurethane.

17. The photochromic article of claim 16 wherein the total photochromic substance is present in an amount of from about 0.15 to 0.35 milligrams per square centimeter of organic host material surface to which the photochromic substance(s) has been applied.

18. The photochromic article of claim 17 wherein the weight ratios of the first photochromic substance to the naphthoxazine compound is from about 1:3 to about 3:1.

19. The photochromic article of claim 18 wherein the article is an ophthalmic lens.

* * * * *